(12) United States Patent
Singer

(10) Patent No.: US 6,534,266 B1
(45) Date of Patent: Mar. 18, 2003

(54) ASSAY OF TRANSCRIPTION SITES BY MULTI-FLUOR FISH

(75) Inventor: Robert H. Singer, New York, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 0 days.

(21) Appl. No.: 09/556,134

(22) Filed: Apr. 21, 2000

Related U.S. Application Data

(60) Provisional application No. 60/130,563, filed on Apr. 22, 1999.

(51) Int. Cl.[7] .................... C12Q 1/68; G01N 33/53; C07H 21/04
(52) U.S. Cl. .................... 435/6; 435/7.2; 435/7.21; 435/174; 536/23.1; 536/24.3; 536/24.31; 536/26.6
(58) Field of Search .................... 435/6, 7.2, 174, 435/7.21; 536/24.3, 23.1, 24.31, 26.6

(56) References Cited

U.S. PATENT DOCUMENTS

| | | | |
|---|---|---|---|
| 5,192,980 A | * | 3/1993 | Dixon et al. ................ 356/326 |
| 5,866,331 A | | 2/1999 | Singer et al. |
| 6,228,575 B1 | * | 5/2001 | Gingeras et al. ............... 435/5 |

FOREIGN PATENT DOCUMENTS

| | | |
|---|---|---|
| EP | 0 612 851 A1 | 8/1994 |
| WO | WO 97/14816 | 4/1997 |
| WO | WO 97/23648 | 7/1997 |
| WO | WO 97/40191 A | 10/1997 |

OTHER PUBLICATIONS

Femino et al. "Visualization of Single RNA Transcripts in Situ" Science, Apr. 1998, 280: 585–590.*

Speicher et al. "Karyotyping human chromosomes by combinatorial multi–fluor FISH" Nature Genetics, Apr. 1996, 12: 368–375.*

Kislauskis et al. "Isoform–specific 3'untranslated sequence sort a–cardia and b–cytoplasmic actin messenger RNAs to different cytoplasmic compartments" J of Cell Biology, 1993, 123(1): 165–172.*

Egholm et al. "PNA hybridizes to complementary oligonucleotides obeying the Watson–Crick hydrogen–bonding rules" Nature, 1993, 365: 566–568.*

Dauwerse et al., "Multiple colors by fluorescence in situ hybridization using ratio–labelled DNA probes created a molecular karyotype," Human Molecular Genetics 1(8):593–595, 1992.

(List continued on next page.)

Primary Examiner—W. Gary Jones
Assistant Examiner—B J Forman
(74) Attorney, Agent, or Firm—Fish & Richardson P.C.

(57) ABSTRACT

An in situ hybridization method for detecting and specifically identifying transcription of a multiplicity of different target sequences in a cell is disclosed. The method includes assigning a different bar code to at least five target sequences, with each target sequence containing at least one predetermined subsequence. Each bar code contains at least one fluorochrome, and at least one bar code comprises at least two different, spectrally distinguishable fluorochromes. A probe set specific for each target sequence is provided in the method. Each probe set contains a hybridization probe complementary to each subsequence in the target sequence. Each probe is labeled with a fluorochrome, and the fluorochromes in each probe set collectively correspond to the bar code for the target sequence of that probe set.

18 Claims, 5 Drawing Sheets

= distinct fluorochromes

= distinguishable target (bar code)

OTHER PUBLICATIONS

Lengauer et al., "Chromosomal bar codes produced by multicolor fluorescence in situ hybridization with multiple YAC clones and whole chromosome painting probes," Human Molecular Genetics 2(5):505–512, 1993.

Augenlicht et al., "Expression of Cloned Sequences in Biopsies of Human Colonic Tissue and in Colonic Carcinoma Cells Induced to Differentiate in Vitro," Cancer Research 47:6017–6021 (1987).

Bonner et al., "Laser Capture Microdissection: Molecular Analysis of Tissue," Science 278:1481–1483 (1997).

Carrington et al., "Superresolution Three–Dimensional Images of Fluorescence in Cells with Minimal Light Exposure," Science 268:1483–1486 (1995).

Femino et al., "Visualization of Single RNA Transcripts in Situ," Science 280:585–590 (1998).

Fung et al., "Spectral Imaging in Preconception/Preimplantatin Genetic Diagnosis of Aneuploidy: Multicolor, Multichromosome Screening of Single Cells," J. of Assisted Reproduction and Genetics 15:323–330 (1998).

He et al., "Identification of c–MYC as a Target of the APC Pathway," Science 281:1509–1512 (1998).

Kononen et al., "Tissue Microarrays for High–Throughput Molecular Profiling of Tumor Specimens," Nature Medicine 4:844–847 (1998).

Lawrence et al., "Highly Localized Tracks of Specific Transcripts within Interphase Nuclei Visualized by In Situ Hybridization," Cell 57:493–502 (1989).

Lawrence et al., "Interphase and Metaphase Resolution of Different Distances within the Human Dystrophin Gene," Science 249:928–932 (1989).

Lawrence et al., "Sensitive, High–Resolution Chromatin and Chromosome Maping In Situ: Presence and Orientation of Two Closely Integrated Copies of EBV in a Lymphoma Line," Cell 60: 51–61 (1987).

Long et al., "Mating Type Switching in Yeast Controlled by Asymmetric Localization of ASH1 mRNA," Science 277:383–387 (1997).

Schena et al., "Quantitative Monitoring of Gene Expression Patterns with A Complementary DNA Microarray," Science 270:467–270 (1995).

Schrock et al., "Multicolor Spectral Karyotyping of Human Chromosomes," Science 273:494–497 (1996).

Simone et al., "Laser–Capture Microdissection: Opening the Microscopic Fronter to Molecular Analysis," TIG 14:272–277 (1998).

Speicher et al., "The Coloring of Cytogenetics," Nature Medicine 2:1046–1048 (1996).

Speicher et al., "Karyotyping Human Chromosomes by Combinatorial Multi–Fluor FISH," Nature Genetics 12:368–375 (1996).

Wickware, "Action at the Edges in Cancer Research," Nature 392:417–420 (1998).

Zhang et al., "Gene Expression Profiles in Normal and Cancer Cells," Science 276:1268–1272.

* cited by examiner

Qualitative Detection $$T_{qual} = n + \left[\sum_{r=2}^{n-1} \frac{n!}{r!(n-r)!}\right] + 1$$

| n = number of distinct fluorochromes | T = number of distinguishable targets | number of unique probes |
|---|---|---|
| 1 | 1 | 1 |
| 2 | 3 | 4 |
| 3 | 7 | 12 |
| 4 | 15 | 32 |
| 5 | 31 | 80 |
| 6 | 63 | 192 |
| 7 | 127 | 448 |
| 8 | 255 | 1024 |
| 9 | 511 | 2304 |

FIG. 2

Quantitative Detection

$$T_{quant} = \sum_{r=1}^{n}\left[\frac{(m+r-1)!}{r!(m-1)!} - m\right] + n + 1$$

T = number of distinguishable targets using unique stoichiometries of each fluorescently labeled probe (eg 2:2 is not used because it is a multiple of 1:1)

| n = number of distinct fluorochromes \ T | m = maximum number of probes per target | | | | | |
|---|---|---|---|---|---|---|
| | 2 | 3 | 4 | 5 | 6 | 7 |
| 2 | 4 | 6 | 8 | 13 | 14 | 24 |
| 3 | 7 | 14 | 23 | 44 | 57 | 102 |
| 4 | 11 | 27 | 52 | 110 | 166 | 306 |
| 5 | 16 | 46 | 101 | 232 | 397 | 762 |
| 6 | 22 | 72 | 177 | 438 | 834 | 1680 |
| 7 | 29 | 106 | 288 | 764 | 1597 | 3390 |

FIG. 4

ASSAY OF TRANSCRIPTION SITES BY MULTI-FLUOR FISH

CROSS REFERENCE TO RELATED APPLICATION

This application claims benefit of provisional application Ser. No. 60/130,563, filed Apr. 22, 1999.

STATEMENT AS TO FEDERALLY SPONSORED RESEARCH

Work on this invention was supported by NIH Grant No. GM 54887. Therefore, the federal government has certain rights in the invention.

BACKGROUND OF THE INVENTION

Recent research on differential gene expression has compared overall gene expression in cancer cells with overall gene expression in normal counterpart cells (Zhang et al., 1998, *Science* 276:1268–1272). Similarly, overall gene expression has been compared in cells undergoing different developmental programs (Chu et al., 1998, *Science* 282:699–705). In such studies, it has been found that large numbers of genes are differentially expressed. For example, more than 500 transcripts are expressed at significantly different levels in cancer cells versus normal cells. In the case of cancer cells, it will be important to correlate the sequences identified as differentially expressed with actual events occurring at the cellular level or tissue level.

SUMMARY OF THE INVENTION

The invention provides an in situ hybridization method for detecting and specifically identifying transcription of a multiplicity of different target sequences in a cell. The method includes assigning a different bar code to at least five target sequences, with each target sequence containing at least one predetermined subsequence. Each bar code contains at least one fluorochrome, and at least one bar code comprises at least two different, spectrally distinguishable fluorochromes. A probe set specific for each target sequence is provided in the method. Each probe set contains a hybridization probe complementary to each subsequence in the target sequence. Each probe is labeled with a fluorochrome, and the fluorochromes in each probe set collectively correspond to the bar code for the target sequence of that probe set. The cell is contacted with a hybridization fluid containing a probe set specific for each target sequence. Following in situ hybridization, fluorochromes on the hybridized probe sets are detected, and spectrally distinguished. This provides separate detection of the transcription site of each target sequence being expressed. The fluorochromes present at each detected transcription site are related to a bar code, which identifies the target sequence at that transcription site.

Target sequences can include 3 or more, e.g., 4, 5, 6, or 7 predetermined, nonoverlapping subsequences. In some embodiments, at least one target sequence contains subsequences having lengths and spacing between each other so that the stoichiometry of fluorochromes on probes hybridized with the target sequence is determinable by quantitative fluorescence detection. This can be achieved, for example, by with each subsequence being 30 to 70 nucleotides long, and all the subsequences clustered within a 100–800 nucleotide segment of the target sequence. The region of clustering can be smaller, e.g., 200–600 nucleotides or 300–500 nucleotides. In some embodiments, each subsequence is about 50 nucleotides long, and all the subsequences are clustered within a 300-nucleotide segment of the target sequence. For maximization of total fluorescence intensity per transcription site, the 100–800 nucleotide segment is located in the 5'-most one third, or 5'-most quarter of the target sequence. Preferably, hybridization probes are labeled with fluorophores attached at intervals of about 5–10 nucleotides. Examples of fluorochromes useful in the invention are Cy2, fluorX, Cy3, Cy3.5, Cy5, Cy5.5, Cy7, fluorescein and Texas red. In some embodiments of the invention, a spectral imagining microscope is employed. Typically the cell is in interphase. The hybridization probe can be an oligonucleotide or a protein nucleic acid (PNA).

The invention also provides a probe set panel. The panel contains at least five probe sets, with each probe set being specific for a different target sequence, each of which contains at least one subsequence. Each probe set contains a hybridization probe complementary to each subsequence in the target sequence for which that probe set is specific. Each probe is labeled with a fluorochrome, so that the fluorochromes in each probe set collectively correspond to a bar code for the target sequence of that probe set.

As used herein, "bar code" means the predetermined, unique combination of fluorochromes assigned to a target sequence.

As used herein, "fluorochrome" means a particular fluorescent dye, e.g., Cy3, without regard to number of individual dye molecules, and without regard to chemical conjugation.

As used herein, "fluorophore" means an individual fluorescent dye molecule or conjugated moiety.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description and the claims.

BRIEF DESCRIPTION OF THE DRAWINGS

FIG. 2 is a table showing the number of bar codes (distinguishable targets) possible (Tqual) when the number of fluorochromes is from 1 to 9 fluorochromes, and qualitative detection is used. The formula for Tqual is also shown.

FIG. 4 is a table showing the number of bar codes (distinguishable targets) possible (Tquant) when the number of fluorochromes is from 1 to 7 fluorochromes, the maximum number of probes (and subsequences) per target sequence is three. The formula for Tquant is also shown.

DETAILED DESCRIPTION

The invention provides a method for specifically assessing the expression of a large number of genes at one time point, in a single cell. This is achieved by simultaneous in situ hybridization of numerous fluorochrome-labelled probes. Through identification codes based on fluorescence color combinations ("bar codes"), the method allows identification of a large number of target sequences in an interphase nucleus, while using only a small number of spectrally distinguishable fluorochrome labels. For example, by using up to five different hybridization probes per target sequence, where each probe is labeled with one of five different fluorochromes, the expression of 31 different genes can be detected and identified, using a qualitative fluorescence detection system, i.e., one not capable of determining fluorochrome stoichiometry. When a quantitative fluorescence detection system is employed, i.e., one that determines fluorochrome stoichiometry, expression of up to 232 different target sequences (genes) can be detected and identified, when only five fluorochromes are employed, with up to five probes per target sequence. The invention can be used to assay the level of gene expression (transcription), ranging from no expression to very high-level expression.

Bar Codes and Fluorochromes

Distinguishing and identifying hundreds of different transcription sites in a single nucleus is achieved through the use of a relatively small number of spectrally distinguishable fluorochromes. Each hybridization probe is specific for a subsequence within a target sequence, and each probe is labeled with a fluorochrome. A probe set is designed for each target sequence. A probe set can consist of a single probe. Following in situ hybridization, the transcription site of each target sequence "lights up" (fluoresces) with a predetermined, unique combination of colors.

Unlike the familiar black and white bar codes read by laser scanners, the colors (fluorochromes) in the "bar codes" of the invention need not appear in any particular order relative to one another. In other words, the encoded information resides in the combinations of colors (and optionally in ratios of color intensity), not in the sequence of the colors.

Figure 1:
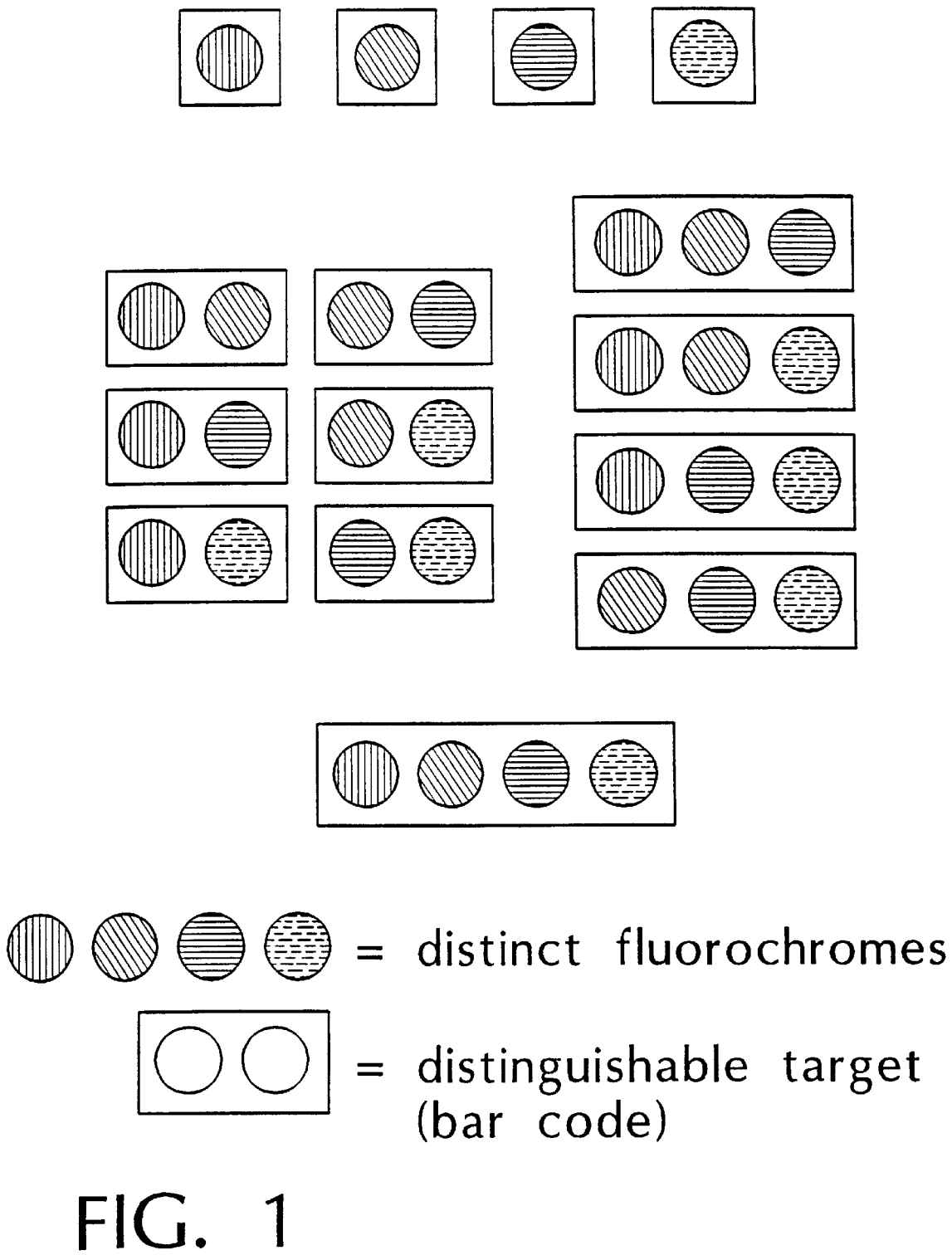
FIG. 1 is a schematic diagram illustrating the generation of 15 qualitative bar codes using four spectrally distinguishable fluorochromes.

In some embodiments of the invention, the detection of fluorochromes on probes hybridized to target sequences is qualitative, i.e., not quantitative. FIG. 1 schematically illustrates how 15 different bar codes can be generated, and thus 15 different targets can be distinguished, when 4 fluorochromes are used. FIG. 2 shows the formula for Tqual, i.e., the number of target sequences that can be identified when using a given number of spectrally distinguishable fluorochromes and qualitative detection. Also in FIG. 2 is a table of values generated using the Tqual formula. The table in FIG. 2 shows, for example, that when using 5 fluorochromes and qualitative detection, up to 31 target sequences can be distinguished.

Figure 3:
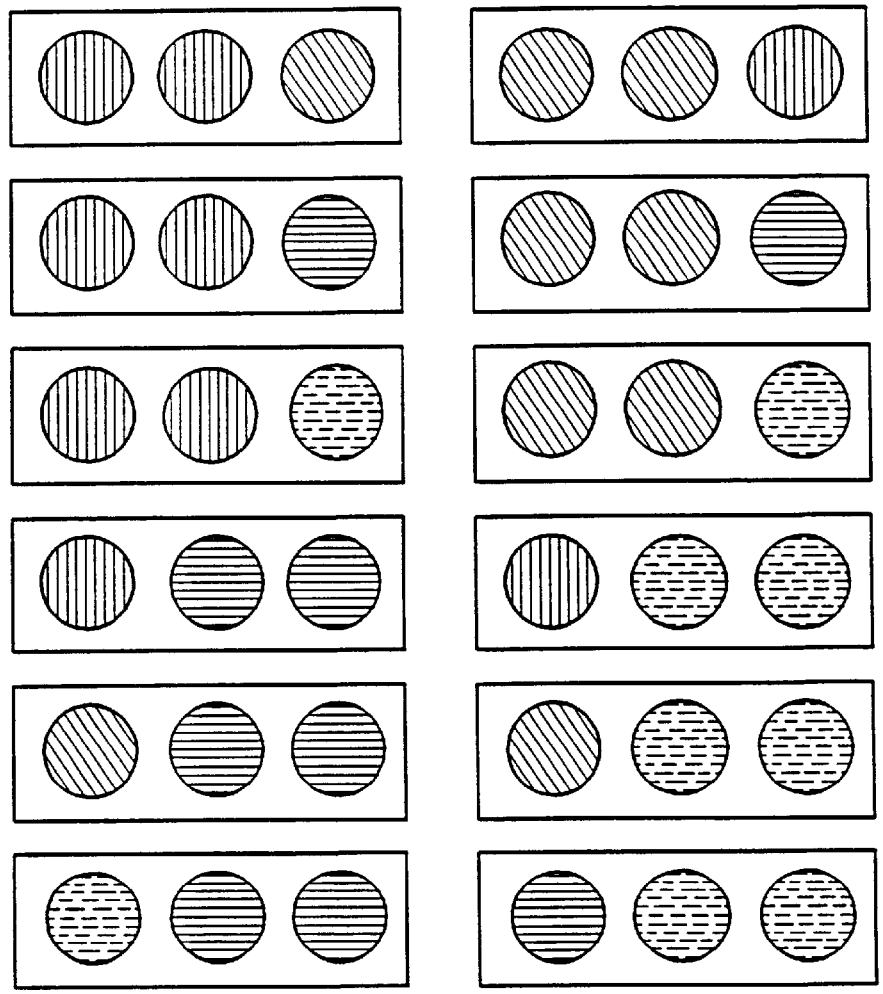
FIG. 3 is a schematic diagram illustrating the generation of 27 quantitative bar codes using four spectrally distinguishable fluorochromes and a maximum of three probes (and subsequences) per target sequence.

In some embodiments of the invention, detection of fluorochromes on probes hybridized to target sequences is quantitative. FIG. 3 schematically illustrates how 12 additional bar codes can be generated, giving a total of 27 different bar codes, when quantitative detection is employed with the same 4 fluorochromes. FIG. 4 shows the formula for Tquant, i.e., the number of target sequences that can be identified when using a given number of spectrally distinguishable fluorochromes with quantitative detection. The Tquant formula is written to remove redundant stoichiometries. For example, 2:2 is not used, because it is a multiple of 1:1. Also in FIG. 4 is a table of values generated using the Tquant formula. FIG. 4 shows, for example, that when using 5 fluorochromes and quanitative detection, up to 31 target sequences can be distinguished.

The difference between qualitative detection and quantitative detection in the invention is illustrated by the following example. With qualitative detection, a target sequence displaying one red fluorochrome and one green fluorochrome would not be distinguishable from a target sequence displaying two red fluorochromes and one green fluorochrome. Both would display the combination of red and green. With quantitative detection, a target sequence displaying one red fluorochrome and one green fluorochrome (red:green stoichiometry=1:1) would be distinguishable from a target sequence displaying two red fluorochromes and one green fluorochrome (red:green stoichiometry=2:1). The targets would be distinguished by differing ratios of red fluorescence intensity to green fluorescence intensity.

There must always be two colors present to determine the ratio between labeled probes. Absolute quantitation alone is not sufficient. For example, there would be no distinction between a transcription site with two red-labeled probes hybridized to each nascent RNA chain, and a site with twice as many nascent RNA chains bearing only one labeled probe per chain. Similarly, a stoichiometry of 1:1 would not be distinguishable from 2:2, 1:2 would not be distinguishable from 2:4, etc. In general, if the quantitative detection allows differentiation among 1 to 3 probes of each color, the number of distinguishable target sequences increases exponentially (FIGS. 2 and 4).

If subsequences (sites where fluorochromes are bound through probe hybridization) are widely spaced within the target sequence, a fluorochrome intensity ratio observed at a transcription site may not accurately reflect the quantitative bar code for that target sequence. For example, a single red-labeled probe hyridizing near the 5' end of the target sequence, and a single green-labeled probe hybridizing near the 3' end of the target sequence, might yield a red:green ratio of 2:1. In each nascent chain, the 5'-located subsequence at which the red-labeled probe binds is transcribed significantly sooner than the 3'-located subsequence at which the green-labeled probe binds. A consequence of this temporal effect can be many more, e.g., twice as many, red-labeled probes bound, in comparison with green-labeled probes, even when the bar code for that target sequence has a red:green stoichiometry of 1:1.

This probe location effect (temporal effect) can be minimized by clustering all of the subsequences within one region of the target sequence. Therefore, in quantitative detection-type embodiments of the invention, it is preferable to use clustered subsequences. In other words, it is preferable to minimize the distance between subsequences. When five 50-nucleotide probes are clustered within a region of 250, 300 or even 400 nucleotides in a target sequence, the fluorochrome stoichiometry in the bar code will predominate over location effects, so that up 232 target sequences will be distinguishable. Even in qualitative detection-type embodiments it may be advantageous to use clustered subsequences in order to obtain similar signal intensities for each of the fluorochromes at a given target sequence, i.e., in a given bar code. For maximimum total fluorescence signal intensity per transcription site, subsequences are clustered in the 5' portion of the target sequence.

Figure 5:
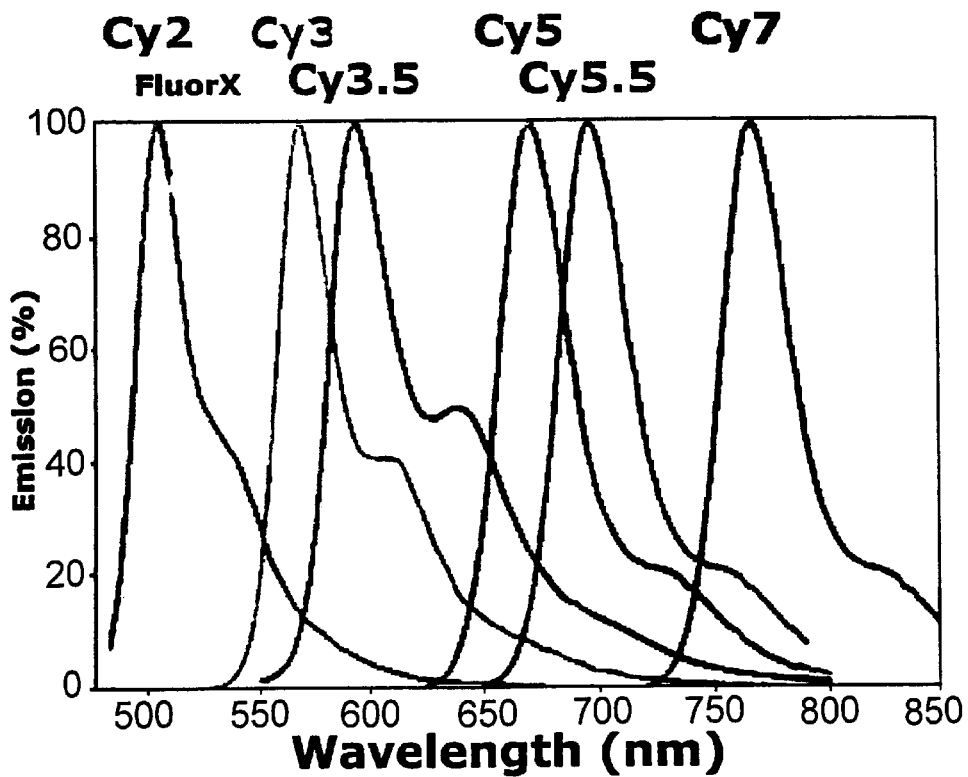
FIG. 5 is a graph showing the emission spectra of seven fluorochromes (fluorescent dyes) that can be used in the invention. The emission spectra shown are those of Cy2, FluorX, Cy3, Cy3.5, Cy5, Cy5.5, and Cy7.

A wide variety of fluorochromes can be used in the invention. The choice of fluorochromes is not critical, as long as: (1) their emission spectra fall within a suitable range of wavelengths (typically about 350 to 850 nm); and (2) they can be spectrally distinguished from each other by the imaging system with which they will be used. Specific examples of commercially available, spectrally distinguishable fluorochromes useful in the invention are Cy2, FluorX, Cy3, Cy3.5, Cy5, Cy5.5 and Cy7 (CyDyes Fluorescent Dyes; Amersham Pharmacia Biotech; Piscataway, N.J.). Emission spectra of these exemplary fluorochromes are shown in FIG. 5. Other examples of fluorochromes useful in the invention are 6-FAM, HEX, NED, ROX, R110, JOE and TAMRA583.

Probe Design and Synthesis

The basic principles of oligonucleotide probe design and synthesis are known in the art. Those basic principles apply generally to the design and synthesis of oligonucleotide probes used in this invention. Similarly, the basic principles of protein nucleic acid (PNA) probe design and synthesis are known in the art, and apply to probes used in this invention.

Each hybridization probe is designed to hybridize with a subsequence of a target sequence. Preferably, the sequence complementarity between each probe and the corresponding subsequence is 100%, but this is not required. In some embodiments, useful sensitivity and specificity may be obtained with less than 100% complementarity, e.g., 90%. Preferably, the G/C content of all the probes are matched so the probes have similar thermal stabilities. There is wide latitude in the choice of hybridization probe length. Considerations in the choice of probe length include total length of target sequence, number of different probes to be accommodated along target sequence, position effect on observed probe stoichiometry, spurious background fluorescence, and fluorescence detection sensitivity. In some embodiments, e.g., embodiments with five nonoverlapping probes hybridized in tandem within a single 250–500 nucleotide region of the target sequence, a suitable probe length is about 50 nucleotides. In some embodiments, different probes within a probe set will have the same length and the same number of fluorochrome moieties per probe molecule, but such uniformity is not required. Preferably, within a subsequence cluster the subsequences are separated from each other by a short stretch of nucleotides, e.g. 10 to about 50 nucleotides.

Methods of synthesizing DNA generally, including oligonucleotide probes useful in this invention, are known in the art. For a general discussion of oligonucleotide synthesis, see Caruthers, "Synthesis of Oligonucleotides and Oligonucleotide Analogs," in *Topics in Molecular and Structural Biology, Vol. 12: Oligodeoxynucleotides* (Cohen, ed.), MacMillan Press, London, pp. 9–24. Machines for automated DNA synthesis are commercially available and can be employed in making suitable probes.

Typically, an oligonucleotide probe used in this invention is obtained in a two step process. The first step is synthesis of an oligonucleotide containing a modified base at each position in the nucleotide sequence where a fluorophore is desired. The second step is covalent attachment of a fluorophore to each modified base.

The modified base provides a functional group through which the fluorophore is covalently attached to the oligonucleotide. The functional group on the modified base can be any suitable functional group, e.g., a primary amino group. The functional group can be located at the end of a spacer arm.

During the synthesis of the oligonucleotide, the functional group on the modified base typically bears a protecting group, e.g., a trifluoroacetamide group. Persons skilled in the art will recognize that the protecting group must be removed by a suitable chemical reaction before the functional group can be used for attachment of a fluorophore.

For preparation of amino modified bases, see, e.g., Jablonski et al. *Nucleic Acids Res.* 14:6115–6128 (1986) and Ruth, *DNA* 3:123 (1984). A suitable modified base is incorporated into a deoxythymidine analog used in automated DNA synthesis, and commercially as "Amino-Modifier C6 dT" (Glen Research, Sterling, Va.). The total number, and the spacing, of fluorophores on the probe can vary. A preferred spacing is one fluorophore every 5–10 bases. For conventional methods of attaching fluorophores onto amino groups, see Agrawal et al. *Nucleic Acids Res.* 14:6227–6245 (1986).

In Situ Hybridization

In situ hybridization methods useful in the invention are well known in the art. See, e.g., Singer et al., 1986, "Optimization of in situ hybridization using isotopic and nonisotopic detection methods," *Biotechniques* 4:230–250; Lawrence et al., 1989, "Highly localized tracks of specific transcripts within interphase nuclei visualized by in situ hybridization," *Cell* 57:493–502; Kislauskis et al., 1993, *J. Cell Biol.* 123:165; and U.S. Pat. No. 5,866,331.

In some embodiments, a single probe is labeled with more than one fluorochrome. For example, a single, relatively long probe labeled with two fluorochromes can replace two relatively short, adjacently-hybridizing probes each labeled with a single fluorochrome.

Image Acquisition and Processing

Persons skilled in the art can carry out the invention using commercially available fluorescence microscopy instrumentation, i.e., optics, digital imaging hardware, computer hardware and computer software. An imaging technology preferred for sensitive, quantitative detection of fluorochromes is described in Femino et al., 1998, "Visualization of Single RNA Transcripts in Situ," *Science* 280:585–590; and in Singer et al., U.S. Pat. No. 5,866,331.

Although the imaging technology employed in some embodiments is capable of visualizing a single mRNA molecule, single molecule sensitivity is not required. That is because numerous nascent RNA transcripts are produced at any actively expressing gene. The nascent RNA transcripts provide highly localized amplification of the target sequence. The degree of gene expression is indicated by total fluorescence intensity at the site. The total fluorescence intensity is positively correlated with the number of hybridized probes, which depends on the number of nascent RNA chains.

The spectral characteristics of transcription sites subjected to in situ hybridization involving fluorochrome bar codes can be determined using any suitable technology. One useful approach to spectral characterization is based on conventional optical bandpass filters. Another approach (discussed below) is spectral imaging microscopy.

Figure 6:
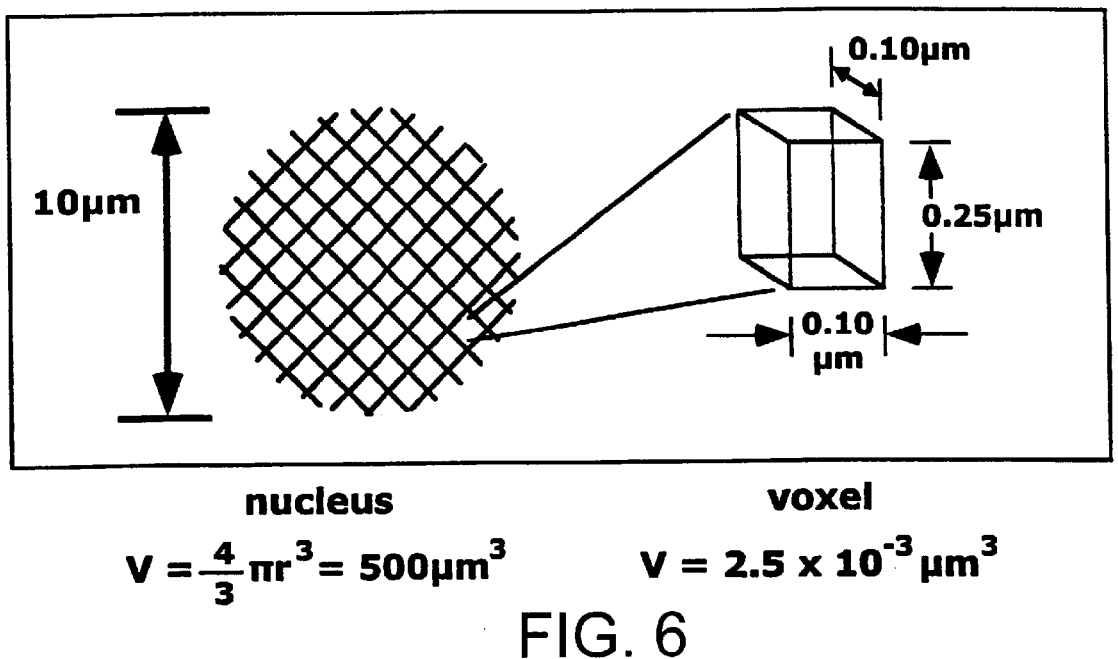
FIG. 6 is a schematic diagram illustrating a voxel and its relationship to nuclear volume.

The invention advantageously exploits the fact that a gene transcription site occupies a very small volume, i.e., approximately of 5 voxels, wherein: 1 voxel=0.1 $\mu$m×0.1 $\mu$m×0.25 $\mu$m=0.0025 $\mu$m$^3$ A 10 $\mu$m diameter nucleus contains a volume of approximately 500 $\mu$m$^3$, i.e., 4/3 $\pi$r$^3$. Thus, the volume of one nucleus is equivalent to approximately 200,000 voxels. One transcription site occupies approximately 1/40,000 of the nuclear volume (FIG. 6). Thus, each transcription site has a distinct location. If two transcription sites are very close, a super-resolution algorithm (Carrington et al., 1995, *Science* 268:1483–1487) which defines the center of density of the fluorescence can compress the transcription into one voxel. This would allow as many as 40,000 transcription sites to be mapped within the nucleus. The spatial resolution of such technology is able to distinguish the expression of every gene in a human cell. This level of spatial resolution is unlikely to be needed, because an individual cell is likely to be expressing no more than 5,000 genes at any moment.

Another imaging technology useful in the invention is spectral imaging microscopy (Schrock et al, 1996, *Science* 273:494–497). This technology combines Fourier spectroscopy, charge-coupled device (CCD) imaging, and optical microscopy to measure simultaneously at all points in the sample emission spectra. The spectral imaging microscope (Applied Spectral Imaging, Inc.; Carlsbad, Calif.) is capable of interrogating the spectral characteristics of each individual pixel in a two-dimensional image.

The 3-dimensional algorithms used in visualization of single RNA transcripts in situ (Femino et al., 1998, *Science* 280:585–590) can be used with spectral imaging microscopy to analyze the spectral character of each transcription site in a 3-dimensional series of images. This approach advantageously distinguishes single discrete spectral signals from the autofluorescence background present in cells and tissue samples. In addition, it achieves high spectral separation, i.e., 15 nm resolution. This increases the number of fluorochromes that can be employed at one time. In addition, the spectral imaging microscope permits greater collection of light output per fluorochrome, as compared to barrier filters, which require a narrow band pass to distinguish signals.

Uses of the Invention

In general, the invention is useful for clinical diagnostic testing and as a research tool in cell biology and molecular genetics. For example, it can be used to diagnose cancer by identifying genes that are differentially expressed in cancer cells, as compared to normal control cells. In addition, a probe set for a particular panel of genes can be used identify a particular type of cancer, to ascertain the cancer's tissue of origin, to predict whether it will be metastatic, or to predict the susceptibility of the cancer to certain drugs. Similarly, a probe set for a genetic disease can be used to determine if a particular genetic disease is present. A probe set for an infectious disease can be used to detect activity of a virus, e.g., HIV or herpes. Probe sets can be used to detect gene expression indicative of hormonal imbalance. In an example of application as a research tool, the invention is useful to confirm, at the single cell level, differential sequence expression data obtained by testing extracted RNA on DNA microarrays (chips).

The invention is further illustrated by the following examples. The examples are provided for illustration purposes only. They are not to be construed as limiting the scope or content of the invention in any way.

EXAMPLES

Example 1

Qualitative Detection

Demonstration of a qualitative detection-type embodiment of the invention is carried out using cells from cultured colorectal (CR) cell lines derived from a human colorectal tumor. These cells are chosen for reasons including the following: They provide an optically optimal model. The nucleus is somewhat flattened in cells spread in culture, but it provides good X-Y spatial discrimination. Considerable molecular genetic characterization is available from previous work on these cells. A high similarity between gene expression profiles of some CR cultured cell lines and CR primary tissue is reported to exist (Zhang et al., 1997, *Science* 276:1268–1272). For example, about half the genes identified by SAGE (serial analysis of gene expression) as overexpressed in primary tumors relative to normal tissue are reported to be increased also in certain colorectal cell lines.

In a first series of experiments, 31 target sequences are chosen, from among sequences previously identified by SAGE analysis as overexpressed in colorectal cell lines relative to normal control cells. Twenty target sequences are chosen because they are thought to exhibit a binary expression pattern, i.e., ten that are off in tumor cells, and on in normal cells, and ten that are on in tumor cells, and off in normal cells. Eleven target sequences are chosen because they are thought to be constitutive in cancer cells and in normal cells.

Using a total of five spectrally distinguishable fluorochromes, 31 different bar codes are created without using a given fluorochrome more than once in a given bar code. The creation of the 31 bar codes using 5 fluorochromes is an extension of the scheme illustrated in FIG. 1, where 15 qualitative bar codes are created using 4 fluorochromes. One of the 31 bar codes is assigned to each of the 31 target sequences.

From one to five 50-nucleotide subsequences clustered near the 5' end of each target sequence are chosen. For each subsequence, a complementary 50-nucleotide probe is chemically synthesized, using an automated DNA synthesizer and commercial reagents, in accordance with the vendors' instructions. Each probe contains five amino-modified bases spaced at ten-nucleotide intervals.

A commercially available cyanine fluorochrome is covalently attached to the amino-modified bases on each probe according to the fluorochrome vendor's instructions. The fluorochrome to be attached to each probe is chosen so that the set of 5 probes for each target sequence collectively contains exactly the same fluorochrome(s) combination present in the bar code assigned to that target sequence.

Fixation of interphase cells and FISH protocol are essentially as described in Femino et al. (*Science* 280:585–590), except that the hybridization fluid contains the fluorochrome-labeled hybridization probes for all of the subsequences in all 31 target sequences.

Following completion of the FISH protocol, interphase nuclei are subjected to fluorescence microscopy, using optical filters essentially as described by Speicher et al., 1996, *Nature Genetics* 12:368–375. In almost all nuclei examined, 21 foci, or elongated tracks, of fluorescence are detected. In some nuclei, two foci appear to overlap. In a few cases, the overlap is too great to allow spectral resolution of the two foci. Although the dimensions and intensities of the foci and tracks vary considerably, it appears that even the smallest and weakest focus or track represents the combined signals from numerous nascent RNA chains at a transcription site. In most nuclei examined, spectral analysis permits the association of each focus or track with one of the 31 bar codes, at a high confidence level.

Example 2

Quantitative Detection

A second series of experiments is carried out. In the second series, five spectrally distinguishable fluorochromes are used to create 232 different bar codes. Many of the bar codes are distinguished from other bar codes only when fluorochrome ratios within combinations are considered. This creation of the 232 bar codes using 5 fluorochromes is an extension of the scheme illustrated in FIG. 3, where 27 quantitative bar codes are created using 4 fluorochromes. One of the 232 bar codes is assigned to each of 232 target sequences.

Cellular material, subsequence selection, probe synthesis, cell fixation, and FISH are carried out as in the first series of experiments described above.

Following completion of the FISH protocol, interphase nuclei are subjected to fluorescence microscopy. The fluorescence microscopy used in this series of experiments combines the methodology of Femino et al. (*Science* 280:585–590) and Singer et al. (U.S. Pat. No. 5,866,331) with the spectral imaging methodology of Schrock et al. (*Science* 273:494–497). This approach to the acquisition and processing of fluorescence information from the hybridized probes provides spectral resolution and signal quantitation sufficient for ascertaining fluorochrome stoichiometry at most transcription sites. In addition, this approach provides 3-dimensional, spatial resolution far greater than that required to resolve 232 transcription sites from each other within the nuclear volume.

Example 3

Correlation of FISH Data with DNA Microarray Data

Data from microarray analysis of RNA isolated from cultured colon cancer cell lines and normal control lines are used to select 31 differentially expressed target sequences. Subsequences are selected, qualitative bar codes are created, labeled probes are synthesized, in situ hybridization is carried out, and fluorescence microscopy is performed, all essentially as described in Example 1 (above). FISH data are used to characterize relative expression levels of the 31 target sequences.

The FISH-derived, relative expression level of each target sequence is compared to the microarray-derived, relative expression level of the same sequence. Even though the identity of the expression product of many of the target sequences is not known, a positive correlation of the FISH data and the microarray data is established.

The comparison shows that a large proportion of sequences indicated by microarray analysis to have a certain expression level in a certain cell type are consistently expressed at the indicated level from cell to cell. The comparison also shows, however, that some sequences indicated by microarray analysis to have a certain expression level are actually expressed at widely varying levels from cell to cell. Such variably-expressed sequences are identified as having relatively little predictive or diagnostic value.

Example 4

Simultaneous Bar Code Detection of Eight Genes in Cultured Cells

Cultured human colon cancer cells (line DLD-1) and cultured human foreskin fibroblast cells were used. Cells were induced with a serum pulse and cycloheximide before preparation, to enhance the transcription sites. Probe sets, i.e., 3 non-overlapping, antisense probes for each target gene, were synthesized using conventional methods and a commercial DNA synthesizer. For subsequent attachment of fluorophores, commercial, modified nucleotides (amino modified C6-DT; Glenn Research, Sterling, Va.) were incorporated during probe synthesis. Each probe was 50 nucleotides in length, and was labeled with five fluorophores.

Each 50-nucleotide probe molecule was labeled with a single type of fluorochrome. For example, the probe set for the β-actin gene or gene transcript (bar code: FITC, cy3, cy5) included the following: (1) a 50-nucleotide probe complementary to a first 50-nucleotide subsequence in the β-actin transcript, and labled with five FITC fluorophores; (2) a 50-nucleotide probe complementary to a second 50-nucleotide subsequence in the β-actin transcript, and labled with five cy3 fluorophores; and (3) a 50-nucleotide probe complementary to a third 50-nucleotide subsequence in the β-actin transcript, and labled with five cy5 fluorophores. The following fluorochromes were used in varying combinations to label the probes and form bar codes: FITC, cy3, cy5, and cy7 (Table 1).

TABLE 1

| Target Gene | Bar Code |
| --- | --- |
| β-actin | FITC, cy3, cy5 |
| c-myc | FITC, FITC, cy3 |
| cyclin D1 | FITC, FITC, cy5 |
| gamma-actin | FITC, FITC, cy7 |
| c-jun | cy3, cy3, cy5 |
| SRF (serum response factor) | cy3, cy3, cy7 |
| COX-2 (cytochrome C oxidase) | cy5, cy5, cy7 |
| c-fos | cy3, cy5, cy7 |

Cultured cells grown on cover slips and treated with TRITON X-100® and fixed with 4% paraformaldehyde for 30 minutes and washed in phosphate buffered saline (PBS). Probe hybridization (30 ng of DNA in each probe set) was carried out under standard conditions, i.e., 50% formamide, 2×SSC, 37° C., for 3 hours. After removal of non-hybridized probes by washing (50% formamide, 2×SSC), cells were mounted on slides in glycerol/phenylinediamine containing DAPI, for viewing by fluorescence microscopy. Imaging of cells was carried out using 60× objective magnification and a CCD camera (Photometrics). Appropriate filter sets were used for each fluorochrome. Images from each filter set were pseudocolored and merged to that one image could be analyzed for overlapping colors at transcription sites. Nuclei were identified by DAPI signal.

Transcription sites of target genes were identified by setting a detection threshold to eliminate weak signals. The transcription sites were the brightest signals in the field. Positive confirmation was determined by the presence of at least two colors at a particular site. A computer programs was written to identify the transcription sites by interrogating bright regions of signal with a prescribed size and pseudocolor identification. The program detected and distinguished transcription at each of the eight target genes within a single sample preparation of colon cancer cells, solely by fluorescence barcode data. In the fibroblasts, similar results were obtained.

Other embodiments are within the following claims.

What is claimed is:

1. An in situ hybridization method for detecting and specifically identifying transcription sites of a multiplicity of at least five different target sequences in a cell nucleus, the method comprising:

assigning a different bar code to the at least five different target sequences, each of the target sequences comprising at least one predetermined subsequence, wherein each bar code comprises at least one fluorochrome, and at least one bar code comprises at least two different, spectrally distinguishable fluorochromes;

providing a probe set specific for each of said at least five different target sequences, each probe set containing a hybridization probe specific for each predetermined subsequence, each hybridization probe consisting of a single nucleic acid molecule comprising a nucleotide sequence complementary to a predetermined subsequence in the target sequence, each probe being labeled with a fluorochrome, wherein the fluorochromes in each probe set collectively identify the bar code for the target sequence of that probe set;

contacting the cell with a probe set specific for each of the at least five target sequences simultaneously such that each hybridization probe hybridizes to the predetermined subsequence to which each hybridization probe is complementary; and detecting fluorochromes on the probe set hybridized to RNA transcribed from each target sequence, if present, thereby separately detecting and specifically identifying transcription sites, wherein the detecting includes spectrally distinguishing the different fluorochromes;

wherein the fluorochromes at a detected transcription site constitute a bar code for the detected transcription site.

2. The method of claim 1, wherein at least one of said at least five target sequences comprises three or more predetermined, nonoverlapping subsequences.

3. The method of claim 2, wherein at least one target sequence contains subsequences having lengths and spacing between each other so that a stoichiometry of fluorochromes on probes hybridized with the at least one of the at least five different target sequences is determinable by quantitative fluorescence detection.

4. The method of claim 3, wherein each subsequence is 30 to 70 nucleotides long, and all the subsequences are clustered within a 100–800 nucleotide segment of the target sequence.

5. The method of claim 4, wherein the subsequences are clustered within a 200–600 nucleotide segment of the target sequence.

6. The method of claim 5, wherein the subsequences are clustered within a 300–500 nucleotide segment of the target sequence.

7. The method of claim 6, wherein each subsequence is about 50 nucleotides long, and all the subsequences are clustered within a 500-nucleotide segment of the target sequence.

8. The method of claim 3, wherein each subsequence is 30 to 70 nucleotides long, and all the subsequences are clustered within a nucleotide segment that represents about 10% of the total target sequence length.

9. The method of claim 4, wherein the 100–800 nucleotide segment is in the 5'-most one third of the target sequence.

10. The method of claim 9, wherein the 100–800 nucleotide segment is in the 5'-most quarter of the target sequence.

11. The method of claim 1, wherein the hybridization probe is labeled with a multiplicity of fluorophores attached at intervals of 5–10 nucleotides.

12. The method of claim 1, wherein the fluorochromes are selected from the group consisting of Cy2, fluorX, Cy3, Cy3.5, Cy5, Cy5.5, Cy7, fluorescein and Texas red.

13. The method of claim 1, wherein fluorochromes are detected using a spectral imaging microscope.

14. The method of claim 1, wherein the cell is in interphase.

15. The method of claim 1, wherein the hybridization probe is an oligonucleotide.

16. The method of claim 1, wherein the hybridization probe is a protein nucleic acid (PNA).

17. The method of claim 1, wherein the cell is part of a tissue sample.

18. The method of claim 1, wherein the fluorochromes are selected from the group consisting of fluorochromes having emission spectra falling between about 350 nm and about 850 nm.

* * * * *